US012810979B2

(12) United States Patent
Soon-Shiong et al.

(10) Patent No.: US 12,810,979 B2
(45) Date of Patent: *Nov. 24, 2026

(54) HEALTHCARE OBJECT RECOGNITION, SYSTEMS AND METHODS

(71) Applicant: Nant Holdings IP, LLC, Culver City, CA (US)

(72) Inventors: Patrick Soon-Shiong, Los Angeles, CA (US); John Zachary Sanborn, Santa Cruz, CA (US); Stephen Charles Benz, Santa Cruz, CA (US); Charles Joseph Vaske, Santa Cruz, CA (US)

(73) Assignee: Nant Holdings IP, LLC, Culver City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/664,373

(22) Filed: Apr. 30, 2026

(65) Prior Publication Data

US 2026/0269034 A1 Sep. 10, 2026

Related U.S. Application Data

(63) Continuation of application No. 19/295,129, filed on Aug. 8, 2025, now Pat. No. 12,658,293, which is a (Continued)

(51) Int. Cl.
*G16H 10/60* (2018.01)
*G16H 40/67* (2018.01)

(52) U.S. Cl.
CPC ............. *G16H 10/60* (2018.01); *G16H 40/67* (2018.01)

(58) Field of Classification Search
CPC ........ G16H 10/60; G16H 15/00; G16H 30/40; G16H 30/20
See application file for complete search history.

(56) References Cited

U.S. PATENT DOCUMENTS

| | | | |
|---|---|---|---|
| 7,016,532 | B2 | 3/2006 | Boncyk et al. |
| 7,403,652 | B2 | 7/2008 | Boncyk et al. |

(Continued)

FOREIGN PATENT DOCUMENTS

| | | | |
|---|---|---|---|
| GB | 2403041 | A | 12/2004 |
| WO | 2005076772 | A2 | 8/2005 |

OTHER PUBLICATIONS

Gossow, David, Peter Decker, and Dietrich Paulus, "An evaluation of open source SURF implementations." Robot Soccer World Cup. Springer, Berlin, Heidelberg, 2010, pp. 169-179.

(Continued)

*Primary Examiner* — Joseph D Burgess
(74) *Attorney, Agent, or Firm* — Harness Dickey & Pierce P.L.C.

(57) ABSTRACT

Healthcare object (HCO) discriminator systems and methods are presented. Systems can obtain a digital representation of a scene via a sensor interface. An HCO discriminator platform analyzes the digital representation to discriminate objects within the scene as being associated with a type of HCO or as being unrelated to a type of HCO. Once the HCO recognition platform determines that a type of HCO is relevant, it instantiates an actual HCO. The HCO can be routed to one or more destinations based on routing rules generated from a template or based on the manner in which the objects in the scene were discriminated.

20 Claims, 4 Drawing Sheets

Related U.S. Application Data continuation of application No. 19/079,691, filed on Mar. 14, 2025, now Pat. No. 12,400,745, which is a continuation of application No. 18/821,076, filed on Aug. 30, 2024, now Pat. No. 12,260,940, which is a continuation of application No. 18/371,885, filed on Sep. 22, 2023, now Pat. No. 12,119,096, which is a continuation of application No. 18/123,578, filed on Mar. 20, 2023, now Pat. No. 11,817,192, which is a continuation of application No. 17/494,608, filed on Oct. 5, 2021, now Pat. No. 11,631,481, which is a continuation of application No. 16/460,325, filed on Jul. 2, 2019, now Pat. No. 11,170,882, which is a continuation of application No. 15/818,249, filed on Nov. 20, 2017, now Pat. No. 10,388,409, which is a continuation of application No. 14/350,048, filed as application No. PCT/US2012/059155 on Oct. 6, 2012, now Pat. No. 9,824,184.

(60) Provisional application No. 61/543,922, filed on Oct. 6, 2011.

(56) References Cited

U.S. PATENT DOCUMENTS

| | | | |
|---|---|---|---|
| 7,477,780 B2 | 1/2009 | Boncyk et al. | |
| 7,565,008 B2 | 7/2009 | Boncyk et al. | |
| 7,627,334 B2 | 12/2009 | Cohen et al. | |
| 7,680,324 B2 | 3/2010 | Boncyk et al. | |
| 7,881,529 B2 | 2/2011 | Boncyk et al. | |
| 7,899,243 B2 | 3/2011 | Boncyk et al. | |
| 7,899,252 B2 | 3/2011 | Boncyk et al. | |
| 7,996,186 B2 | 8/2011 | Nakagawa et al. | |
| 8,218,873 B2 | 7/2012 | Boncyk et al. | |
| 8,224,077 B2 | 7/2012 | Boncyk et al. | |
| 8,224,078 B2 | 7/2012 | Boncyk et al. | |
| 9,824,184 B2 | 11/2017 | Soon-Shiong et al. | |
| 10,388,409 B2 | 8/2019 | Soon-Shiong et al. | |
| 11,170,882 B2 | 11/2021 | Soon-Shiong et al. | |
| 12,087,412 B1 | 9/2024 | Sorkey et al. | |
| 2001/0051879 A1 | 12/2001 | Johnson et al. | |
| 2005/0149360 A1 | 7/2005 | Galperin | |
| 2005/0158767 A1 | 7/2005 | Haskell et al. | |
| 2005/0210044 A1 | 9/2005 | Hills et al. | |
| 2006/0195339 A1 | 8/2006 | Backhaus et al. | |
| 2006/0226957 A1 | 10/2006 | Miller et al. | |
| 2006/0293925 A1 | 12/2006 | Flom | |
| 2007/0065017 A1 | 3/2007 | Kotwaliwale et al. | |
| 2007/0072250 A1 | 3/2007 | Kim et al. | |
| 2007/0239482 A1 | 10/2007 | Finn et al. | |
| 2007/0265533 A1 | 11/2007 | Tran | |
| 2007/0273504 A1 | 11/2007 | Tran | |
| 2007/0276270 A1 | 11/2007 | Tran | |
| 2008/0001735 A1 | 1/2008 | Tran | |
| 2008/0004904 A1* | 1/2008 | Tran | A61B 5/0006 340/286.07 |
| 2008/0077604 A1 | 3/2008 | Bharara | |
| 2008/0147554 A1 | 6/2008 | Stevens et al. | |
| 2008/0170758 A1* | 7/2008 | Johnson | G07C 9/257 382/115 |
| 2009/0005650 A1 | 1/2009 | Angell et al. | |
| 2009/0006125 A1 | 1/2009 | Angell et al. | |
| 2009/0227876 A1 | 9/2009 | Tran | |
| 2009/0227877 A1 | 9/2009 | Tran | |
| 2009/0318779 A1 | 12/2009 | Tran | |
| 2010/0105034 A1 | 4/2010 | Hutton et al. | |
| 2010/0172555 A1 | 7/2010 | Hasezawa et al. | |
| 2010/0309198 A1 | 12/2010 | Kauffmann | |
| 2011/0105034 A1 | 5/2011 | Senders et al. | |
| 2011/0115624 A1 | 5/2011 | Tran | |
| 2011/0122138 A1 | 5/2011 | Schmidt et al. | |
| 2011/0125519 A1 | 5/2011 | Dhoble | |
| 2011/0125521 A1 | 5/2011 | Dhoble | |
| 2011/0133903 A1 | 6/2011 | Alsafadi | |
| 2011/0181422 A1 | 7/2011 | Tran | |
| 2013/0046547 A1 | 2/2013 | Drucker et al. | |
| 2013/0314522 A1 | 11/2013 | Ravid et al. | |
| 2014/0114675 A1 | 4/2014 | Soon-Shiong | |
| 2022/0028508 A1 | 1/2022 | Soon-Shiong et al. | |
| 2024/0013874 A1 | 1/2024 | Soon-Shiong et al. | |
| 2024/0420814 A1 | 12/2024 | Soon-Shiong et al. | |
| 2025/0210164 A1 | 6/2025 | Soon-Shiong et al. | |
| 2025/0364095 A1 | 11/2025 | Soon-Shiong et al. | |

OTHER PUBLICATIONS

Leutenegger, Stefan, Margarita Chli, and Roland Y. Siegwart, "BRISK: Binary robust invariant scalable keypoints." IEEE, 2011, (8 pages).

Lowe, David G., "Object recognition from local scale-invariant features." iccv. Ieee, 1999 (8 pages).

Mikolajczyk, Krystian, and Cordelia Schmid, "A performance evaluation of local descriptors." IEEE transactions on pattern analysis and machine intelligence 27.1O (2005): (34 pages).

Mountney, Peter, et al., "Simultaneous stereoscope localization and soft-tissue mapping for minimal invasive surgery." International Conference on Medical Image Computing and Computer-Assisted Intervention. Springer, Berlin, Heidelberg, 2006, (8 pages).

Office Action issued in Canadian Application No. 2,851,426 dated Apr. 27, 2018, 4 pages.

Chow et al., "Controlling Data in the Cloud: Outsourcing Computation without Outsourcing Control," CCSW 2009, 6 pages.

Li et al., "Fuzzy Keyword Search over Encrypted Data in Cloud Computing," INFOCOM, 2010 Proceedings IEEE, Mar. 14-19, 2010, 5 pages.

"NTT and Mitsubishi Electric Develop Advanced Encryption Scheme to Increase Cloud Computing Security," Nippon Telegraph and Telephone Corporation, NTT News Release, http:i/wv,Nv'.nttco. jpinews20i0/1OO?e/100728a.html, Jul. 28, 2010, 3 pages.

European Search Report issued in European Application No, 12838194.4 dated Jul. 7, 2015, 6 pages.

International Search Report and Written Opinion issued in International Application No. PCT/US2012/059155 dated Dec. 27, 2012, 8 pages.

Office Action from corresponding U.S. Appl. No. 15/818,249 dated Nov. 27, 2018.

Office Action from corresponding U.S. Appl. No. 15/818,249 dated Jun. 19, 2018.

Office Action from corresponding U.S. Appl. No. 15/818,249 dated Feb. 20, 2018.

Office Action from corresponding U.S. Appl. No. 14/350,048 dated Feb. 22, 2017.

Office Action from corresponding U.S. Appl. No. 14/350,048 dated Nov. 3, 2016.

Office Action from corresponding U.S. Appl. No. 14/350,048 dated May 20, 2016.

Office Action from corresponding U.S. Appl. No. 16/460,325 dated Oct. 27, 2020.

* cited by examiner

Object Type
(Drug Template)
243A

- Indexed By (discriminator char.)
  - Size, Dimension
  - Color
  - OCR Text
    - Pill
    - Bottle
    - Packaging
  - Location
  - Etc.
- Attributes
  - Template Type: Drug
  - Template ID: 0x2DC54D
  - Name: <TBD>
  - Generic: <TBD>
  - Manufacture: <TBD>
  - Cost: <TBD>
  - Prescription: <TBD>
  - HCO ID: <GUID>
  - Etc.
- Routing Rules
  - Source: <TBD>
  - Destination(s): <TBD>
    - Doctor: <TBD>
    - Pharmacy: <TBD>
    - Etc.
  - Message: <TBD>
    - "Refill"
    - "Overdose"
    - "Informational"
    - "Compliance"
    - Etc.
  - Priority
  - Urgency
  - Modality
    - Email
    - Phone
    - Text
    - Etc.
  - Etc.

○ ○ ○

Object Type
(Symptom Template)
243N

- Indexed By
  - Face Color
  - Face Features
  - Temperature
  - Etc.
- Attributes
  - Template Type: Symptom
  - Template ID: 0xAE15FD
  - Symptom Name: <TBD>
  - Severity: <TBD>
  - Pain: <1 to 10>
  - Body location: <TBD>
  - HCO ID: <GUID>
  - Gene:
    - Rearrangement
    - Foreign
    - Native
  - Patient:
    - Name: <TBD>
    - ID: <TBD>
- Routing Rules
  - Source: <TBD>
  - Destination: <TBD>
    - Doctor
    - Urgent-care
    - Hospital
    - Etc.
  - Message: <TBD>
    - "Emergency"
    - "Accident"
    - Etc.
  - Priority
  - Urgency
  - Modality
    - Phone
    - Text
    - Video Chat
    - Etc.
  - Etc.

Figure 2

HEALTHCARE OBJECT RECOGNITION, SYSTEMS AND METHODS

This application is a continuation of U.S. application Ser. No. 19/295,129, filed Aug. 8, 2025, which is a continuation of U.S. application Ser. No. 19/079,691, filed Mar. 14, 2025, which is a continuation of U.S. application Ser. No. 18/821,076, filed Aug. 30, 2024, which is a continuation of U.S. application Ser. No. 18/371,885, filed on Sep. 22, 2023, which is a continuation of U.S. application Ser. No. 18/123,578, filed on Mar. 20, 2023, which is a continuation of U.S. application Ser. No. 17/494,608, filed on Oct. 5, 2021, which is a continuation of U.S. application Ser. No. 16/460,325, filed on Jul. 2, 2019, which is a continuation of U.S. application Ser. No. 15/818,249, filed on Nov. 20, 2017, which is a continuation of U.S. application Ser. No. 14/350,048, filed on Apr. 4, 2014, which claims priority to PCT Application No. PCT/US2012/059155, filed on Oct. 6, 2012, which claims priority to U.S. Provisional Application Ser. No. 61/543,922, filed on Oct. 6, 2011. These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is medical information technologies.

BACKGROUND

Existing healthcare systems can collect healthcare data and incorporate the data into medical records. However, known systems assume a priori that data collected is in fact healthcare data and should be incorporated into such data records. Unfortunately, known healthcare systems lack the ability to assimilate raw data and make a determination if the raw data should be considered healthcare data. Rather, healthcare systems merely rely on a priori human knowledge to determine that the data will, in fact, be healthcare data.

Consider for example, U.S. patent application publication 2006/0293925 to Flom titled "System for Storing Medical Records Access Using Patient Biometrics", filed Jun. 20, 2006. Flom contemplates updating medical records using patient biometrics. As biometric data is obtained, corresponding records are updated. Although useful when biometric data is known to be medically related, Flom fails to address conditions where generic or ambient data might or might not be medically related. In the Flom case, the biometric data is a priori determined to be related to medical records.

Another example includes U.S. patent application publication 2007/0365533 to Tran titled "Cuffless Blood Pressure Monitoring Application" filed May 12, 2006. Tran makes further progress by detecting data associated with individuals and detecting if they fall, their facial expressions, or other conditions. As with Flom, Tran assumes the data is a priori related to healthcare. Tran requires data-specific algorithms to determine if a condition is present. Tran also fails to offer insights into discriminating if generic or ambient data is medically relevant or not.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

Thus, there is still a need for systems capable of recognizing that objects are in fact healthcare objects.

SUMMARY OF THE INVENTION

The inventive subject matter provides apparatus, systems and methods in which objects are recognized as related to healthcare objects (HCOs). One aspect of the inventive subject matter includes an HCO discrimination system having a sensor interface and an HCO recognition platform. The sensor interface allows the system to acquire a digital representation of a real-world scene having at least one object (e.g., a person, a collision, a document, a device, etc.). The object recognition platform obtains the digital representation through the sensor interface and determines if objects represented by the digital representation relate to healthcare. The platform preferably comprises an HCO discriminator, which derives one or more discriminator characteristics from the digital representation. The discriminator uses the characteristics to discriminate if one or more objects from the scene represented in the digital representation can be classified as being associated with one or more HCO types (i.e., a type or class of HCO) or not associated with an HCO type. Example HCO types include data objects, a template for example, representing a patient, a healthcare provider, a medical device, a prescription or medication, an insurance claim, a medical record, or other types of healthcare related items. If an object within the digital representation is associated with an HCO type, then an HCO processor produces one or more actual HCOs according to the HCO types and other information available, including the discriminator characteristics. When the HCO is fleshed out or provisioned with necessary attributes, the recognition platform submits the HCO to an HCO router. The router routes the HCO to a destination based on routing rules and provisioned information in the HCO. For example, the router might route the resulting HCOs to a pharmacy, an insurance company, a doctor's office, a medical record data store, a patient, a hospital, an emergency response team, or other entity.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWING

FIG. 2 illustrates possible healthcare object templates that represent a type of healthcare object.

DETAILED DESCRIPTION

It should be noted that any language directed to a computer should be read to include any suitable combination of computing devices, including servers, interfaces, systems, databases, agents, peers, engines, modules, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

One should appreciate that the disclosed techniques provide many advantageous technical effects including generating healthcare objects and configuring a routing infrastructure to route the healthcare object over network to a destination.

The following discussion provides many example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. Further, within the context of this document, the terms "coupled to" and "coupled with" are used euphemistically to mean "communicatively coupled with" where to networked devices are able to communicate with each other over a network, possibly via one or more intermediary devices.

Figure 1:
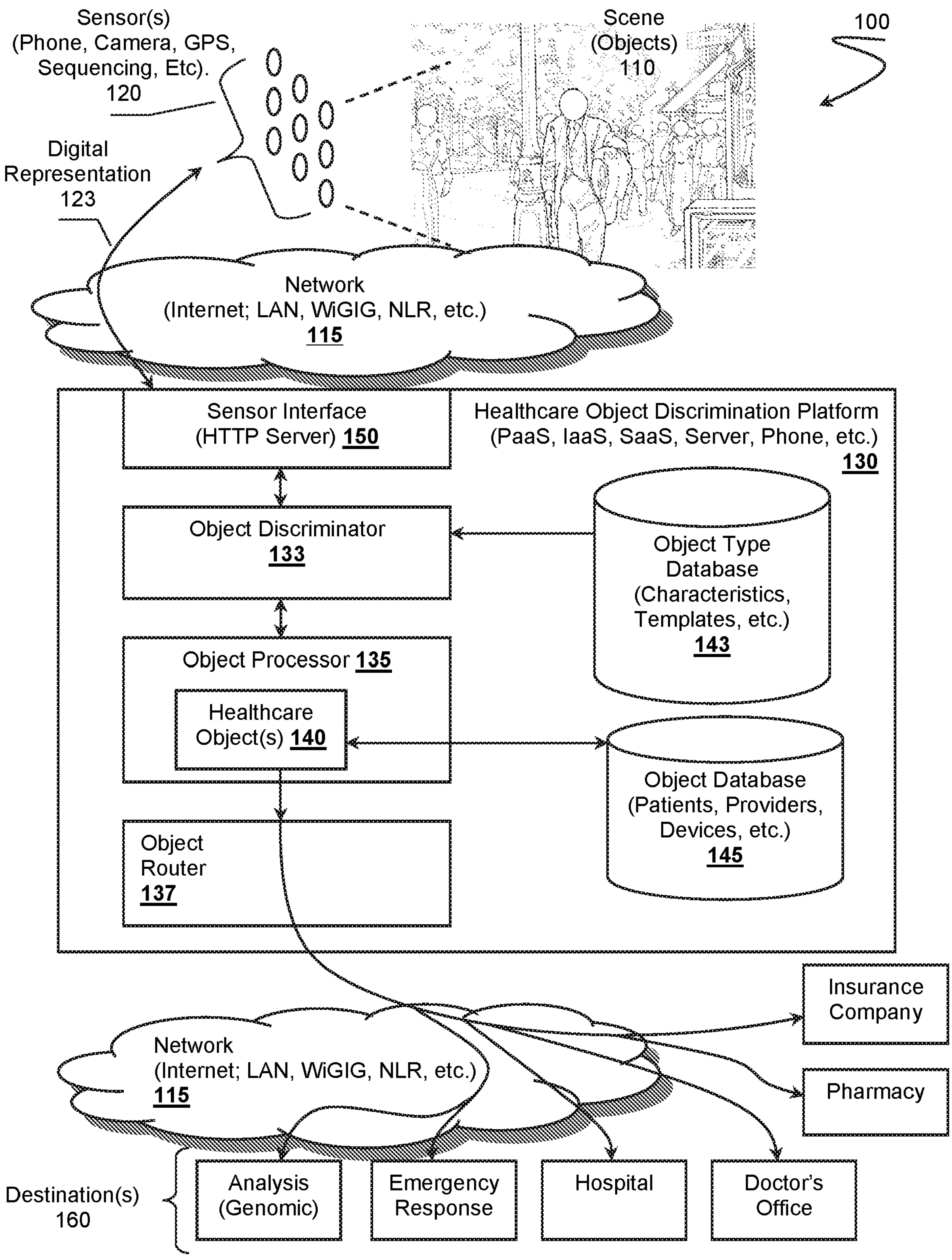
FIG. 1 is a schematic of healthcare object recognition ecosystem.

FIG. 1 illustrates a healthcare object (HCO) recognition ecosystem 100. The example illustrated contemplates that sensor data is acquired from one or more sensors 120, a cell phone for example, which transmits sensor data as digital representation 123 over network 115 (e.g., network to a remote server operating as HCO discrimination platform 130. Platform 130 includes multiple components capable of analyzing digital representation 123, determining if a recognized object in a scene is associated with an HCO type, constructs an HCO, and routes the object to other entities.

One should note that FIG. 1 represents one possible embodiment. The various roles or responsibilities of each component discussed below could be disposed into different devices, local or remote to the scene. For example, a cell phone could operate as the sensor platform comprising sensors 120, include sensor interface 150, and operate as HCO discriminator 133. In other embodiments, the various components can be disposed within a cloud-based computing environment possibly as a Platform-as-a-Service (PaaS), Infrastructure-as-a-Service (IaaS), Software-as-a-Service (SaaS). It is also contemplated that the various roles or responsibilities could be disposed within networking infrastructure including routers, switches, gateways, access points, or other infrastructure. Example networking infrastructure that could be suitability adapted for use with the inventive subject matter includes the routing nodes disclosed in U.S. Pat. No. 7,603,428 to Wittenschlaeger titled "Software Application Striping", filed on Dec. 18, 2008, where the networking infrastructure operates as a general purpose distributed computing fabric.

One or more sensors 120 acquire data representative of a scene that has one or more objects in scene 110. The acquired data is presented as digital representation 123 and can include data according to one or more data modalities. Thus, objects in scene 110 can be represented by different modalities of data. Example modalities can include image data, video data, audio data, text data, raw sensor data, digitized analog data, or other modalities. Further, digital representation 123 can include other types of data, possibly in the form of metadata representative of other aspects of the environment, the user, or other scene related information. Example additional data that can be included in digital representation 123 can include location data (e.g., GPS, triangulation, etc.), position data, orientation data, heading data (e.g., directional movement, change in altitude, rotational movement, etc.), biometric data, temperature data, security data, encrypted data, or other types of ambient data that can be collected about the scene or environment. Sensors 120 can include a broad spectrum of data collecting devices and can be as varied as the data modalities. Example data collecting devices can include cameras, microphones, accelerometers, magnetometers, bio-sensors, compasses, gyroscopes, thermometers, Hall Effect sensors, medical sensor (e.g., blood pressure, EKG, EEG, perfusion detector, glucose meters, etc.), a user interface, touch screen, or other types of data acquisition devices.

Sensor 120 can include devices associated with an individual, a smart phone perhaps, or third party devices. For example, a person could be in a public location, possibly an airport, bus terminal, shopping mall, or other location when they experience a health crisis. The security system can observe the crisis through a security camera independent of other sensor platforms. Thus, the security system can construct digital representation 123 from its camera feeds.

Objects in scene 110 are illustrated as real-world objects. One should appreciate that other types of objects can participate in ecosystem 100. For example, in some embodiments the objects in scene 110 can include virtual objects that persist within ecosystem 100. Example virtual objects can include messages on a virtual bulletin board bound to a real-world object, game objects (e.g., players, characters, goals, objectives, rewards, items, etc.), or other items that can exist in a virtual state. Consider a scenario where a game player is playing an augmented reality game that mixes virtual objects in a real-world setting. During a strenuous game session the player might experience difficulty breathing due to exertion and might encounter a virtual construct that represents a phobia of the game player. The phobia coupled with exertion might cause the game player to enter a critical health state. In response, ecosystem 100 can send digital representation 123, which includes information about the virtual construct, to platform 130 for analysis and dissemination to appropriate destinations 160.

Digital representation 123 is transmitted or otherwise sent to HCO recognition platform 130 over network 115. The nature of network 115 can depend on the nature of the sensor platform. For example, when a cell phone captures digital representation 123, network 115 could include a cellular network or the Internet. In some embodiments, network 115 can include a dedicated medical network, the National Lamba Rail (see URL www.nlr.net) for example. Other examples of network 115 include a Local Area Network (LAN), a Wide Area Network (WAN), a Personal Area Network (PAN), Virtual Private Network (VPN), a mesh network, a peer-to-peer network, or other types of networks. Network 115 can be based on various suitable protocols or infrastructure, possibly including one or more of the following protocols: cellular (e.g., GSM, CMDA, etc.), 802.11, WiGIG, Zigbee, Bluetooth, USB, Ethernet, ATM, or other suitable protocols.

The communication between HCO recognition platform 130 and sensors 120 can be bi-directional. As platform 130 analyzes digital representation 123 to determine if it has data relevant to healthcare objects, platform 130 can determine if additional data would be required. For example, platform 130 could request a cell phone user to capture additional images or video of scene 110 for further clarity, or to capture medically-relevant information (e.g., heart rate, respiration rate, etc.). Consider a scenario where a user observes that a person collapses. The user sends an image of the fallen person to platform 130. Platform 130 recognizes the person as having a heart condition. In response, platform 130 causes the user's cell phone to render a user interface that requests the user to take the fallen person's pulse. The user can enter the pulse information within the user interface and submit it back to platform 130. In some embodiments, the user interface is rendered in real-time under command from HCO recognition platform 130, possibly through a browser or even a dedicated application.

HCO recognition platform 130 can include one or more of sensor interface 150 through which the system can acquire digital representation 123 of scene 110 and the associated objects. In the example shown, sensor interface 150 comprises a web server capable of receiving packaged data possibly in the form of HTTP messages (e.g., XML, WSDL, etc.). It should be appreciated that sensor interface 150 could also include a direct connection to the sensors through a wired connection (e.g., CAN, SPI, GPIB, RS-232, Ethernet, Firewire, USB, serial lines, data lines, etc.) or a wireless connection (e.g., Zigbee, Bluetooth, WiMAX, UMTS, Wi-Fi, 802.11, 802.15, 802.16, radio, IrDA, etc.).

HCO recognition platform 130 preferably comprises HCO discriminator 133 communicatively coupled with the sensor interface 150. HCO discriminator 133 obtains digital representation 123 via sensor interface 150 and begins an analysis of digital representation 123. Digital representation 123 can comprise raw data, encapsulated data, encrypted data, or data as a file. For example, digital representation 123 can be received by HCO discriminator 133 in the form of an XML file including metadata describing the environment of scene 110 (e.g., time stamps, location data, user ID, etc.) as well as encapsulated raw data (e.g., image data, audio data, etc.).

HCO discriminator 133 can take on different forms as is the case with other components in the system. In some embodiments, HCO discriminator 133 comprises a cloud-based computing environment offering its services to other components of ecosystem 100. Further, HCO discriminator 133 could comprise a mobile device (e.g., vehicle, cell phone, mobile kiosk, medical cart, etc.) or even a sensor platform hosting sensors 120. In other embodiments, HCO discriminator 133 could include one or more remote servers.

HCO discriminator 133 applies one or more analysis algorithms to digital representation 123 to derive one or more discriminator characteristics. The discriminator algorithms vary depending on the modality of data within digital representation 123. For example, when digital representation 123 includes image data, the algorithm can include Scale Invariant Feature Transform (SIFT; Lowe, David G. (1999). "Object recognition from local scale-invariant features." Proceedings of the International Conference on Computer Vision. 2. pp. 1150-1157), Gradient Location and Orientation Histogram (GLOW; Krystian Mikolajczyk and Cordelia Schmid "A performance evaluation of local descriptors", IEEE Transactions on Pattern Analysis and Machine Intelligence, 10, 27, pp 1615-1630, 2005), Binary Robust Invariant Scalable Keypoints (BRISK; Lutete al. et al. "BRISK: Binary Robust Invariant Scalable Keypoints" Proceedings of the IEEE International Conference on Computer Vision (ICCV) 2011), Speeded Up Robust Feature (SURF; David Gossow, Peter Decker and Dietrich Paulus, "An Evaluation of Open Source SURF Implementations", Lecture Notes in Computer Science, 2011, Volume 6556/2011, 169-179) or other image processing techniques. If the digital representation includes video image, the algorithms might comprise Simultaneous Localization and Mapping (SLAM; Mountney, P.; Stoyanov, D. Davison, A. Yang, G-Z. (2006). "Simultaneous Stereoscope Localization and Soft-Tissue Mapping for Minimal Invasive Surgery." MICCAI 1: 347-354) or vSLAM to track objects or identify objects within a scene. Audio data can be analyzed using speech recognition algorithms (e.g., Hiddien Markov Models, Support Vector Machines, etc.), sound recognition (e.g., see CoreLogger® by Audio Analytics), or other types of audio recognition techniques. Additional algorithms can include optical character recognition; those disclosed in U.S. Pat. No. 7,016,532; OpenCV; Dynamic time warping; or others that are known or yet to be invented. Regardless of the modality, HCO discriminator 133 compiles one or more discriminator characteristics from digital representation 123.

The digital characteristics from digital representation 123 reflect attributes of digital representation 123, scene 110, objects in scene 110, or other aspects of the environment. In some embodiments, discriminator characteristics represent measurements or metrics stored in digital representation 123. In an example where digital representation 123 includes an image, the digital characteristics could include light balance, color balance, color histograms, radial invariant features, or other image data characteristics. Further, the discriminator characteristics could also include attributes associated with objects possibly including color, interpreted symbols (e.g., bar codes, alphanumeric, etc.), facial recognition parameters, voice recognition parameters, location parameters, sensor parameters, image parameters, motion parameters, or other scene related parameters. Each modality of data could result in different derived discriminator characteristics.

The discriminator characteristics can be represented according to different techniques. In some embodiments, a set of discriminator characteristics associated with scene 110 can include a vector where each member of the vector corresponds to a specific dimension or modality of data. For example, the first element of the vector could represent a listing of relevant image features, while the second element of the vector could represent a listing of relevant audio features, and yet a third element might represent OCRed text discovered within digital representation 123. The vector of discriminator characteristics can have any number of practical dimensions. In other embodiments, the set of discriminator characteristics can be represented as an N-tuple where each element of the N-tuple includes an attribute name along with one or more corresponding values.

HCO discriminator 133 uses the discriminator characteristics to discriminate if real-world objects in scene 110 are or are not associated with a type of healthcare object as stored in object type database 143. In some embodiments, discriminator 133 can recognize a real-world object in scene 110 and provision a temporary object with information related to the recognized real-world object. For example, discriminator 133 could recognize a face in scene 110 as a person. In response, discriminator 133 creates a temporary object that is provisioned with attributes, possibly from a known object database 145 of known real-world objects or object information. The attributes, or even discriminator characteristics, of the temporary object can be compared to known HCO types stored in object type database 132. If the temporary object's attributes and attributes of known HCO types satisfy matching criteria, then the temporary object can be considered associated with the HCO type.

One should note that temporary objects are not required. Contemplated systems could also include an HCO type database 143 storing known HCO types, possibly in the form of templates. One should appreciate that the "type of object" is, itself, a distinct manageable data object. For example, object type database 143 can store many templates where each template represents an HCO type. Example HCO types can include a patient, a healthcare provider, a symptom, a drug, a medicine, a prescription, an X-ray, an image, a medical image, a victim, a diagnosis, a prognosis, a rendered service, a report, or other types of classes of HCOs.

The HCO types can be indexed in HCO type database 143 according to one or more discrimination characteristics. Each HCO type can have an associated signature of discriminator characteristics considered relevant to the HCO type. In some embodiments, the signature can be considered a contextual relevance for circumstance under which the HCO type should be considered relevant. The signature of discriminator characteristics can be based on the different modalities of data: sounds, colors, temperatures, or other parameters derived from digital representation 123. When the derived discriminator characteristics satisfies HCO type matching criteria with respect to discriminator characteristics, then corresponding objects in scene 110 can be considered associated with an HCO type.

In some embodiments, the attributes, characteristics, parameters, or other types of discriminators are normalized or mapped to a common namespace to allow for easy comparisons. Thus, object type database 143 can store HCO types as indexed within the namespace. Once discriminator 133 derives a set of discriminator characteristics associated with digital representation 123, discriminator 133 can construct a query for object type database 143 based on the set of discriminator characteristics. In response to receiving the query, object type database 143 can return a result set including HCO types that are considered to satisfy the query through comparing the HCO type's signature to the query requirements or optional conditions. The result set can include one or more HCO types. Thus, object discriminator 133 can discriminate among objects in the scene and obtain templates for an HCO.

Regardless of how objects in scene 110 are compared to HCO types, one should appreciate that the disclosed discriminators can track how a scene object was discriminated or recognized as being associated with an HCO type (e.g., by image, by sound, by movement, by location, by combination of modalities, etc.). Further, discriminator 133 can also derive one or more confidence levels, or error measurements, indicating a degree of the discrimination either as being associated with an HCO type or as not being associated with an HCO type. The confidence levels can be calculated based on number of matching criterion, weightings, or other factors; resulting in a measure of how well a scene object was discriminated. The inventive subject matter is considered to include using the measure of discrimination to provision, build, route, interact with, or otherwise manage an HCO upon instantiation. The measure of discrimination could be multi-valued, possibly where each value represents a different aspect of the discrimination. Contemplated aspects an indication of certainty of a person's identity, an indication of a type of circumstance (e.g., urgent, accident, life-threatening, etc.), or other indications.

If at least one of the objects in scene 110 has been discriminated from others as begin associated with an HCO type, HCO discriminator 133 can pass information derived about the object and HCO type to HCO processor 135. HCO processor 135 converts the various parts of the information into one or more actual HCOs 140. In some embodiments, the HCO type information could be accompanied by an HCO template to be populated by the system. HCO processor 135 uses use the template to further provision an actual HCO according to the template or rules associated with the corresponding HCO type. Further, the HCO processor 135 can leverage the discriminator characteristics to provision the actual HCO. Thus, HCO processor instantiates or otherwise produces the actual HCO 140. Once instantiated, HCO 140 becomes a persistent object in ecosystem 100. In some embodiments, HCO 140 can be a permanent object, an electronic medical record data entry for example. While in other embodiments, HCO 140 can be transient in time or location, where HCO 140 can be deleted or deactivated once conditions are met. HCO 140 can be configured with a time limit or can be configured to be deactivated upon consumption by a recipient.

Consider a scenario where a traffic camera observes an automobile accident on a highway in winter, HCO processor 135 could produce an emergency response request as an HCO 140 and transmit HCO 140 to a paramedic team. HCO 140 can include a current temperature at the site with an indication of a likelihood of hypothermia, a time of the accident, an estimated location of the accident, make or model of the car, license plate number, possibly a recognized face, victim's information, or other information. Still further, possibly based on the license plate number and assuming a face was not recognized, the HCO processor can determine a car owner and possibly family physician information. HCO processor 135 can produce a second HCO 140 comprising a notification having information obtained from the scene to be sent to a family physician. Thus, HCO processor 135 can instantiate multiple HCOs 140 from digital representation 123.

HCOs 140 can be provisioned with a broad spectrum of information based on the information available about scene 110, scene objects, HCO types, or other factors. Examples could include provisioning HCOs 140 based various HCO types including a symptom, an image, a drug, a healthcare provider, a patient, a rendered service, a report, an insurance claim, a drug trial report, a procedure or other HCO types. The actual HCO 140 can carry very specific detailed information provisioned based on one or more fields defined within the corresponding HCO type, possibly where the HCO type comprises a template. Further, HCO 140 can be provisioned with one or more destination attributes, possibly including routing rules, indicating where or how HCO 140 should be routed. The destination attributes can be derived from attributes from the HCO type or from information obtained from objects in known object database 145 (e.g., a person, building, etc.). One should further appreciate that HCO 140 can also be stored in object database 145 for future use or later retrieval.

Once an HCO 140 is produced, HCO 140 can be passed to HCO router 137. Router 137 consults one or more routing rules based on information from HCO 140, or other sources, and routes HCO 140 to one or more destinations 160, possibly over a network 115 (e.g., LAN, WAN, UWB, cell, National Lambda Rail (see URL www.nlr.net), Internet, etc.). In some embodiments, HCO 140 can comprise the routing rules. Contemplated destinations 160 can include emergency response entities, hospitals, a doctor's office or phone, pharmacies, insurance companies, family members, emergency medical record warehouses, remote specialists, a storage device, a patient's account, or other type of healthcare provider device or facility. HCO 140 can also be encrypted to protect privacy and decrypted upon reception assuming proper validation or authentication of the recipient. Further, a level of encryption or security applied can be determined by the discrimination measure of the corresponding scene object. If only generic information were available about the corresponding object, the discriminator measure might have a low certainty that the scene object is associated with a specific identity; therefore, minimal security would be required if any at all.

As discussed previously, HCOs 140 can represent a wide range of object types. For example, HCO 140 can include an object representing aspects of a person's or other entity's genome. HCO 140 can comprise a representation of a person's genome, a genomic sequence (e.g., DNA), RNA or RNA sequence, a kinome, or other genetic representations. In some embodiments, the digital representation of a person's genome can be obtained from a genomic analysis device capable of deriving genomic data from a blood sample. Example devices could employ Polymerase Chain Reaction (PCR) to generate a DNA segment signal. It is contemplated an HCO 140 could include a visual representation of an entity's genomic information. Genomic HCOs can be routed to destination 160 comprising a remote analysis engine for development of personalized treatment, which could drive kinase inhibitor drug development.

Consider a scenario where sensors 120 include a genomic sequencing system that generates one or more DNA segment signals as represented by digital representation 123. Suitable sequencing systems capable of generating genomic segment signals can include those offered by PerkinElmer® (see URL www.perkinelmer.com), 454 Sequencing® (see URL www.454.com), or even genome analysis systems soon to be offered by Five3 Genomics® (see URL www.five3genomics.com). HCO discriminator platform 130 observes the genomic signals and can determine that portions of the represented genomic information can include one or more genomic HCO types. The HCO types can be obtained from HCO type database 143 by comparing the information in the genomic signals to the indexing attributes of the HCO types in HCO type database 143.

Contemplated genomic HCO types can represent different aspects of genomic information. Example genomic HCO types can include native sequences, foreign sequences, altered sequences, or other types of genomic objects. A native sequence can be considered genomic information that is known to be from the source of the genetic sample (e.g., human, animal, blood, biopsy, etc.). For example, known object database 145 can include known genomic information of a baseline model. The baseline model could be based on the individual from whom the sample is obtained, possibly taken at an earlier different time; from a reference population; or from a canonical or statistical reference. HCO discriminator platform 130 can determine that a sequence is native by comparing the information in digital representation 123 to the genomic information in object database 145 thereby allowing platform 130 to create a native genomic HCO 140.

A foreign sequence can be detected via similar techniques to determining a native sequence. In the case of determining that a genomic sequence is foreign, HCO discriminator platform 130 determines that the genomic signal is non-native by failing to find similar sequences associated with the sample provider, or by finding a corresponding sequence from a different source; a bacteria, a virus, a different person, a different animal, or other source. Such an approach is considered advantageous because it gives rise to the ability to determine if the sample provider suffers from an infection or other ailment even before the symptoms of the ailment appear. As a more concrete example, a blood sample can be analyzed via sensors 120 and could be determined to contain anthrax genetic material. In response, HCO 140 could comprise an anthrax infection diagnosis, which can then be routed to a healthcare provider or even the CDC. The foreign sequence information can be used to instantiate or produce HCO 140 representative of the foreign sequence.

An altered sequence can be considered a sequence that appears to be modified in some form. The altered sequence could include a rearrangement of genomic material, a mutation, insertions, deletions, or other types of alterations. For example, HCO discriminator platform 130 could determine that the altered sequence could comprise the host's own genetic sequence, but occurring in unexpected locations. Such rearrangements can include inter-chromosomal rearrangements or intra-chromosomal rearrangements. The altered sequences can comprise an indication of cancer.

Corresponding instantiated genomic HCOs 140 can include additional data relating to the genomic information from digital representation 123, which can aid in routing HCO 140 to an appropriate destination. Example, information can include rearrangement information as discussed above, copy number, allele fraction number, variants, mutations, known gene information, or other genomic information. Known gene or mutation information could be obtained from genomic databases, possibly including the UCSC known gene database or COSMIC mutation database from the Sanger Institute. Such information can directly influence routing rules for the corresponding HCO 140. For example, the copy number can be used to route HCO 140 to proper analysis facilities or through a change of analysis nodes. Alternatively, the known gene or mutation information can be used to ensure the corresponding HCO 140 is routed as a proper facility, the CDC for example as mentioned above.

FIG. 2 provides possible examples of HCO type 243A through 243N, collectively referred to as HCO types 243. In the example shown, HCO type 243A represents a drug type of object, while HCO type 243N represents a symptom type of object. HCO types 243 are presented as templates.

The templates can be stored in a corresponding HCO type database, object type database 143 in FIG. 1 for example, where the templates are indexed by discriminator characteristics. In the example shown, HCO type 243 is indexed by several salient features including size, dimensions, color, OCRed text, location (e.g., GPS, address, etc.), among other characteristics. The symptom template can be retrieved according to other discriminator characteristics that are more relevant to symptoms. HCO type 243N is indexed by face features, face color, temperature, or other factors that might be considered relevant to a symptom. Each HCO type 243 can be indexed according to other features, as necessary.

One should appreciate that although only two templates are presented, the ecosystem can support any number of HCO type 243. Further, HCO types 243 can be linked to each other to form more complex HCO types 243. For example, a base template might represent a face where HCO type 234N points to or incorporates the face HCO type. Such an approach is considered advantageous because it allows for users to create complex HCO types without requiring the user to define new types from scratch.

HCO types 243 can be classified according to one or more classification schemes as defined with respect to the derived discriminator characteristic. Each class can have a defined name that determines the class and have class criteria used to determine if the HCO types 243 are relevant to circumstances associated with the scene. The class criteria can be defined in terms of a namespace associated with the discriminator characteristics. For example, HCO types 243 could belong to a class "vehicle accident" where the class criteria for "vehicle accidents" require location coordinates be associated with known highway locations. Thus, when the digital representation includes a highway location, the HCO recognition platform can search the HCO type database for HCO types 243 that are indexed by the classification or indexed by the discriminator characteristics; highway locations in this case.

HCO types 243 can also include attributes or other properties that describe the nature of the corresponding type of object. Some attributes can be pre-populated with type-specific information. In the example shown, HCO types 243 include permanent attributes including a template type name, and a template ID (e.g., a GUID, UUID, etc.). HCO types 243 could include any number of permanent attributes. The attributes can further include non-populated attributes that are to be populated upon instantiation of a corresponding HCO. The nature of the attributes can be quite varied. The attributes can also be constructed according to one or more standards to aid in integrated with other types of HCOs. For example, the attributes can conform to medical standards for electronic medical records (e.g., HL7, ANSI X12, CEN, DICOM, ASTM CCR, etc.).

An especially interesting type of attributes includes routing rules as illustrated. Each HCO type 243 can also include one or more routing rules that govern how the resulting instantiated HCO should be routed to one or more destinations. The routing rules, similar to attributes per se, can include permanent values or values to be populated upon instantiation. For example, a source address might always reference the HCO recognition platform's address. However, it is contemplated that the source address could also be populated during instantiation to align with a patient's address, a municipality address, a cell phone number or address, or other source identifier. Destination addresses can be similarly populated. Although each template is illustrated as having a single source and a single destination, one should appreciate that HCOs could include multiple sources or multiple destinations.

Source and destination addresses can be populated according to the modality under which the corresponding HCO is to be routed. For Internet communications, the addresses can comprise IP addresses, ULRs, URIs, email addresses, web services APIs, or other types of Internet protocol addresses. Other types of addresses correspond to the nature of the communication and can include phone numbers, database commands, traditional mail addresses, electronic medical record interface addresses, fax numbers, document object identifiers (DOIs), or other types of addresses. Examples techniques relating to DOIs that can be adapted for use with the inventive subject matter include those described in co-owned International application having serial number PCT/US12/30060 titled "Healthcare Management Objects" filed on Mar. 22, 2012.

Figure 3:
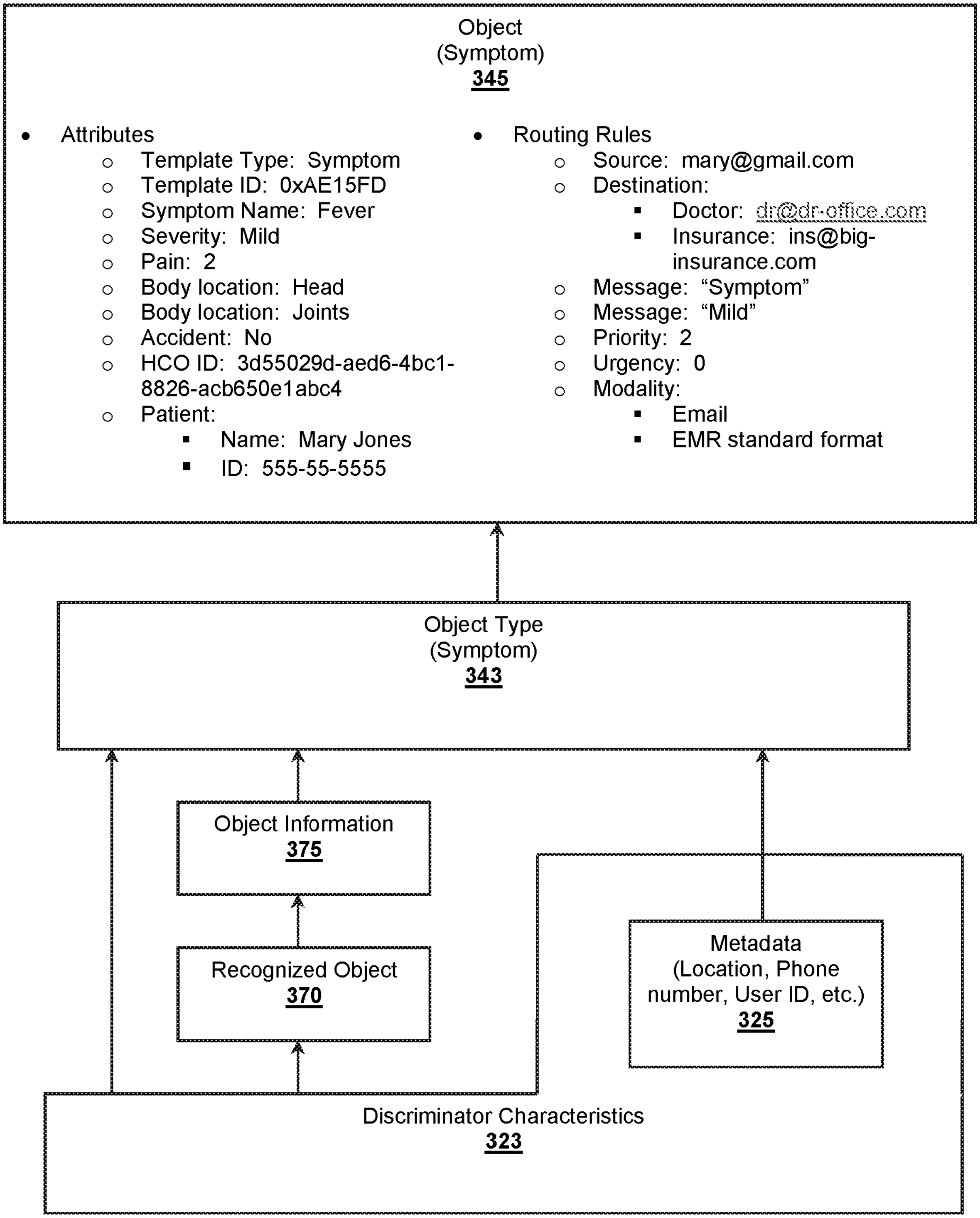
FIG. 3 illustrates a flow of information to instantiate or to produce a healthcare object.

FIG. 3 illustrates populated HCO 345 produced or instantiated based on the symptom template and illustrates information flow to produce HCO 345. In the example shown, the recognition platform derives or otherwise acquires discriminator characteristics 323 from analysis of the digital representation of the scene. The information from discriminator characteristic 323 is available for populating HCO type 343.

HCO 345 can be instantiated by the platform based on one or more information sources. In the example shown, the attributes of HCO 345 can be populated from information directly obtained from discriminator characteristics 323. For example, the attributes can include values relating to image data, possibly based on color values in the image, color distributions, or other image features. Further, the attributes can include values obtained from audio or even OCRed text. Perhaps, in this example, Mary Jones has been in an accident and a first responder images her driver's license. In response, the platform OCRs the text of the driver's license and populates corresponding attributes from HCO type 343 to create HCO 345.

An additional information source can include metadata 325 that might be associated with discriminator characteristics 323. The metadata can be part of a digital representation of the scene or obtained through other sources. Metadata 325 is considered to include information about the circumstances, entities involved with the circumstances, or other information that falls outside the boundaries of the analysis algorithms assigned to deriving discriminator characteristics 323. Examples of metadata 325 could include location data, user identity information (e.g., phone number, social security number, name, etc.), name of witnesses, security keys or tokens, medical history, or other information. Although metadata 325 is illustrated as composing discriminator characteristics 323, one should appreciate that metadata 325 can be obtained through external sources, possibly through a query to a public or private search engine. A public search engine could include social networks (e.g., Facebook®, LinkedIn, etc.) while a private search engine could include an electronic medical record system (e.g., healthcare provider's database, an insurance provider database, a genome database, etc.). Regardless of where metadata 325 originates, the information it supplies to the platform enables the platform to populate the HCO type 343 to create HCO 345.

Yet another somewhat indirect source of information includes recognized object 370. As the platform derives discriminator characteristics 323, it can use them to identify one or more recognized objects 370. Once recognized, the recognition platform can obtain object information 375 or other types of content information related to recognized object 370. For example, the recognition platform can use facial recognition features or other biometric information to identify a person as recognized object 370. Once the person is recognized, the platform can obtain information, object information 375, related to the person to populate HCO 345. Example techniques that can be adapted to obtain object information 375 or other content information includes those disclosed in U.S. Pat. Nos. 7,016,532; 7,403,652; 7,477,780; 7,680,324; 7,565,008; 7,899,243; 7,881,529; 7,899,252; 8,224,077; 8,224,078 and 8,218,873.

Yet another example information source can include a Mechanical Turk (MTurk) system (not shown). As a digital representation is fed into the recognition platform, portions or all of the digital representation can be sent to the MTurk system for review. The MTurk system can construct one or more tasks for human beings to review the digital representation to obtain additional information. For example, in scenarios where the recognition platform might have difficulty understanding a context of a scene, perhaps a scene of an accident, the MTurk system can request a review of a scene image and request the humans behind the MTurk to identify the scene as being an accident scene or not an accident scene. The information resulting from the MTurk can then be folded into HCO 345 by populating fields of HCO type 343. An example MTurk system that could be employed for use with the inventive subject matter can include the Amazon® Mechanical Turk (see URL www.mturk.com)

In view that an MTurk system might not necessarily generate accurate results, the HCO ecosystem can employ one or more techniques to mitigate the risk of poor results. One technique includes submitting multiple MTurk tasks to review the same digital representation. In response, the HCO recognition platform can evaluate the statistics resulting from the MTurk evaluation of the digital representation. Consider the example shown with respect to HCO 345. Perhaps the digital representation includes an image of a patient, possibly the patient's face. The HCO recognition platform can submit the image to the MTurk system and request one or more evaluations of the image data where the MTurk creates one hundred tasks per evaluation. One evaluation might include a determination if the image indicates the scene is or is not an accident. The recognition platform might receive 95 "No" results and 5 "Yes" results indicating the image is more than likely not an accident. The accident example yields a binary result (i.e., yes or no), but might also include a confidence level derived from the statistics of the results. The results from the survey can also fall on a spectrum. Another evaluation might request a determination of pain on a person's face on a scale of one to ten. In such cases, the results would likely include a distribution of values from one to ten. In the example, shown the pain has been evaluated with a value of "2", but could also include additional information from the MTurk results such as a width of the distribution around the value of "2".

Regardless of the source of information for populating HCO type 343, the platform instantiates or otherwise produces HCO 345 from the information available. One should appreciate that not all attributes of HCO 345 require values. In some embodiments, HCO type 343 can indicate which attributes are considered conditional information rather than required information. Consider scenarios where privacy might be of concern. A person's name might be withheld for privacy concerns, perhaps in an emergency situation. Still, in other situations a person's name might be absolutely required, possibly when treating a symptom and historical medical history is required.

HCO 345 represents a symptom and includes two main sets of properties. The first set labeled "Attributes" is presented as examples of information that describe the nature or features of HCO 345. The second set of properties is labeled "Routing Rules" to indicate that the corresponding attribute information relates to the routing nature of HCO 345. The attributes can include a broad spectrum of information that can be used to manage HCO 345 or provide information to a recipient of HCO 345. Management information can include an HCO type indicator, a template ID, an HCO ID represented as a GUID, an object name, an object type, a classification, indices for later retrieval, or other types of information. Content that can be considered informational for a recipient can include the object name (e.g., symptom), a severity, point, body locations, patient information, CPT codes, ICD codes, HCPCS codes, or other informational items.

The routing rules are specifically shown to indicate that HCO 345 can incorporate specific information governing how HCO 245 should be disseminated through the ecosystem. As discussed earlier, the routing rules can include source or destination address information. In this specific example, the source and destination addresses include email addresses. One should note that HCO 345 includes multiple destinations. Additional routing information can include priority indicators, urgency indictors, modalities, or even message information for the recipient or routing infrastructure. In view that the symptom associated with HCO 345 is a fever with a mild severity, the priority has been defined as low with no urgency. Also note that the modality of the HCO can also include an EMR standard format.

The routing rules can further include specific routing information beyond a destination address. Additional routing rules can include a chain of recipients, quality of service requirements, required time of delivery, computation requirements along a route if any; security tokens or keys, certificates, or other types of routing information that can affect delivery of HCO 345 to a recipient.

One should appreciate that routing rules can be constructed based on how HCO 345 was discriminated from others in the scene. For example, the priority, urgency, or even destination can be dictated according to the rules within HCO type 343 applied to how discriminator characteristics 323 were derived or evaluated. Application of such rules is considered an advantageous approach over simply recognizing objects per se. One advantage is that the modality of the data available can govern which routing rules should be applied to ensure HCO 345 is appropriately routed to destination.

Once instantiated HCO 345 can be packaged for delivery. HCO 345 is presented as a listing of information. One should appreciate that HCO 345 can be packaged according to various techniques, again possibly depending on the modality of the delivery mechanism. For example, HCO 345 can be packaged as an XML file having tags representing the attributes or routing rules. In other embodiments, HCO 345 could include a binary format ready for placement into an EMR database. Along similar lines, HCO 345 can be encapsulated within a database command for entry into a database (e.g., an SQL command). Once packaged, HCO 345 can be routed to the corresponding destinations.

Figure 4:
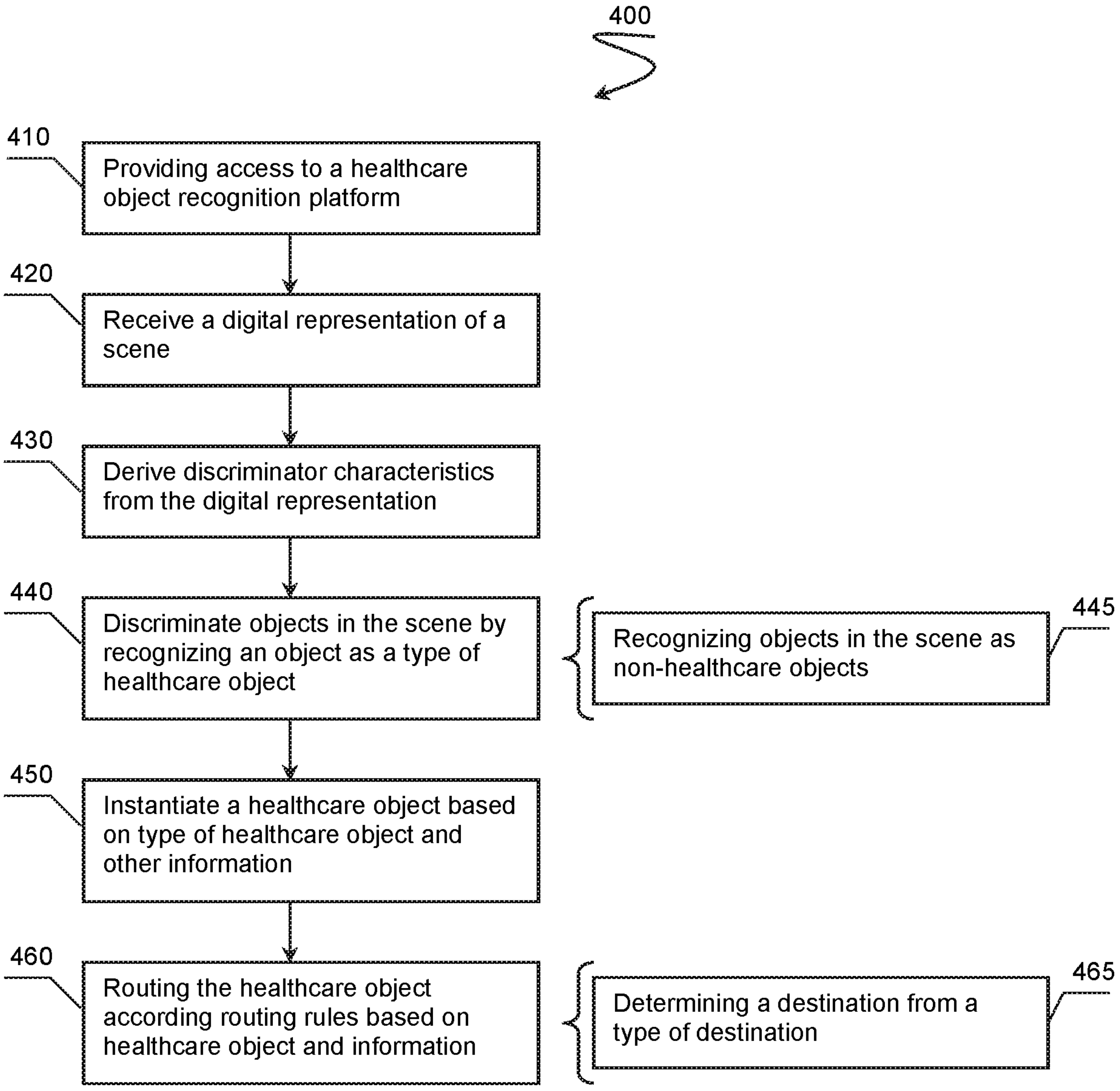
FIG. 4 is a schematic of a method for constructing and routing a healthcare object.

FIG. 4 illustrates method 400 of routing HCOs. Step 410 includes providing access to an HCO recognition platform. In some embodiments the HCO recognition platform operates as an ambient public or private service, possibly based on a search engine. For example, the Google® search engine could be suitably adapted to operate as the HCO recognition platform. In such a scenario, digital representations of a scene or objects can be submitted easily to the platform without requiring a dedicated application on a computer or smart phone. In other embodiments, the platform can operate as a for-fee service that users pay for possibly based on a subscription basis, per use charge, or other form of charge. In other embodiments, the HCO recognition platform could also include a dedicated application available to one or more computing devices. In such cases, the HCO recognition can include an app installed on a user's smart phone, tablet, computer, workstation, server, kiosk, virtual servers (e.g., cloud, etc.) appliance, set top box, game console, or other computing device. Still further the roles or responsibility of the HCO recognition platform can be distributed across multiple devices, even including networking infrastructure (e.g., switches, routers, gateways, etc.).

Providing access to the HCO recognition platform can include integrating the features of the platform's services within existing infrastructure. For example, the platform's services can be integrated within 911 or E911 services to ensure HCOs can be constructed and routed to appropriate recipients without latency of requiring a human to conduct data entry tasks. Additional examples could include integration with video communications, telepresence infrastructure, or augmented reality infrastructure. As users increasingly use Skype®, Facetime®, or even Layar® AR-based interfaces, it is expected that such information can be used to construct appropriate HCOs, subject to appropriate authentication or authorization. Consider a scenario where a community leverages Skype for communication. An HCO integrated with Skype can create HCOs representative of psychological profiles of the users without attaching private information to the profiles. The psychological profiles can be routed to researchers or appropriate psychologists for review.

Step 420 includes receiving a digital representation of a scene. The digital representation can be acquired through various techniques. In some embodiments, the digital representation is pushed from one or more sensor platforms, a cell phone or security camera for example. In such cases, a person can acquire audio data, image data, video data, or other types of data modalities with their cell phones. The scene data can then be sent to the HCO recognition platform regardless of whether the platform is local to the cell phone or distal to the cell phone. In other embodiments, the digital representation can be pulled from the sensor platforms. For example, the HCO recognition platform can request or control the sensor platform to acquire the digital representation. Consider a scenario where a person captures a still image of an accident scene. The still image can be pushed to the HCO recognition platform. In response, the HCO recognition platform can command the person's cell phone to capture audio or video of the scene in an attempt to gather additional data. Still, further the digital representation can be acquired through ambient collection of available sensor feeds relevant to the scene once suitable authentication or authorization has been acquired.

Step 430 can include deriving one or more discriminator characteristic from the digital representation. The discriminator characteristics can be derived through one or more algorithms as discusses previously and can comprise one or more algorithmic results (e.g., audio signatures, SIFT features, BRISK features, vSLAM coordinates, etc.). The discriminator characteristics can cover a broad spectrum of information relating to the digital representation itself. For example, the discriminator characteristics can represent data constructs representative of the data from the digital representation itself, a SIFT feature for example. Further, the discriminator characteristics can also include data that more closely relates to the scene, facial recognition parameters, OCRed text, voice recognition parameters, sensor parameters (e.g., sensor data, position, orientation, measures, metric, etc.), or other types of parameters. Yet further, the discriminator characteristics can include metadata describing the nature of the scene. Example metadata can include user identities, GPS location, time stamps, security tokens, or the aspects related to the scene.

Step 440 can include discriminating scene objects by recognizing an object in the scene as an HCO type. The HCO recognition platform utilizes the discriminator characteristics to identify one or more HCO types. As discussed above, the platform can construct to query targeting an HCO type database storing one or more templates for HCOs. The query can be based on a namespace defined in terms of discriminator characteristic where the HCO types are stored according to an index scheme in the same namespace. For example, the HCO types could include a symptom template that is based on facial recognition features. When the discriminator characteristics include facial recognition parameters, among others, the HCO platform can submit a query to the HCO type database where the query requests HCO types related to faces. In response, the HCO type database could return face-based symptom templates.

One should appreciate that the HCO recognition platform can, in addition to tracking the discriminator characteristics used to discriminate scene objects as HCO types or non-HCOs, track the path taken to arrive at the determination that an HCO type relates to the scene. Such an approach can be considered representative of how objects in the scene are discriminated, or the manner in which the scene objects are discriminated. Providing an understanding of how objects in the scene are discriminated provides additional foundations by which instantiated HCOs are to be routed as discussed below. The path can be represented by a path object that includes indicators of data modalities, algorithms applied, confidence levels, or other factors outlining the process by which objects were discriminated.

As an example, consider a scenario where a digital representation of a scene includes video data. Objects within the scene can be discriminated through several modalities: image data (e.g., SIFT, BRISK, etc.), motion data (e.g., vSLAM techniques), or even audio data (e.g., voice recognition). The recognition platform can determine that some objects in the scene should be considered HCO types. Further, the recognition platform can classify the objects according to the manner in which they are discriminated based on modality type (i.e., image, audio, motion) or even the confidence of the determination. Thus, each HCO type that is returned to the recognition platform can comprise path object data, possibly as metadata tags, which indicates how the objects in the scene were discriminated.

One should further appreciate that objects in the scene can be recognized as non-HCOs as suggested by step 445. Non-HCOs in the scene might provide useful information (e.g., street signs for location information, etc.), but might not map to an HCO type. Therefore, the inventive subject matter is considered to include discrimination of scene objects as being related to a type of HCO or as being unrelated to a type of HCO.

Step 450 includes the HCO recognition platform producing or instantiating an HCO based on the HCO type associated with the scene objects and other information. In embodiments where an HCO type includes a template, the HCO recognition platform can obtain information from the discriminator characteristics, the scene itself, or through object recognition to populate required or optional fields in the template. Once populated, the platform can be considered to have a fully instantiated HCO.

One aspect of producing the HCO includes constructing one or more routing rules for the HCO. The routing rules can be generated according to policies within the template. The policy can itself include fields to be populated, source or destination addresses, for example, that can depend on routing modalities. Further, the routing policies associated with the HCO type can include criteria for establishing the routing rules based on how corresponding objects were discriminated. For example, the routing policies can dictate a destination chain for the HCO. When a confidence level is low with respect to an image modality, the routing rules can be constructed to ensure the HCO is routed to a subject matter expert first before forwarding to a final destination. The routing polices can be used to generate routing rules for the HCO based on the data modalities used for discrimination, the number of modalities, confidence levels, a time or location where discriminator occurs, algorithms used, identification of entities involved with the discrimination, or other factors.

Step 460 includes routing the HCO according to the routing rules configured to operate based on the HCO and other information available (e.g., discriminator characteristics, metadata, etc.). The HCO can be packaged according to a format most amenable to the routing modality. In some embodiments, the HCO is packaged as an EMR possibly based on XML while in other embodiments the HCO might be packaged as an email or a file. Regardless of the packaging, the HCO can be routed by submitting the HCO to an HCO router that can determine one or more destinations for the HCO. As indicated by step 465, the HCO router can determine the destination from information available the HCO recognition platform and possibly based on a destination type. For example, when an HCO comprises an accident report, the HCO might comprise destination types of primary healthcare physician, closest family member, and police. In response, the HCO can be instantiated with the fax number of the physician, email address of the family member, and a call to 911. The specificity of the information can be obtained through recognizing people in the scene, receiving contact information from a victim's cell phone, or public records.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

What is claimed is:

1. A computer-based method of routing healthcare objects, the method comprising:

receiving, by at least one processor from at least one sensor, a digital representation of a scene in an environment;

deriving, by the at least one processor, a set of discriminator characteristics via execution of one or more discriminator algorithms on the digital representation according to data modalities within the digital representation;

tracking, by the at least one processor, a path object associated with the deriving, the path object comprising indicators of data modalities used, algorithms applied, or confidence levels reflecting a process by which objects in the scene were discriminated;

discriminating, by the at least one processor, objects in the scene by recognizing an object as a healthcare object type based on the set of discriminator characteristics;

instantiating, by the at least one processor, a healthcare object from the recognized object according to the healthcare object type;

generating, by the at least one processor, routing rules for the healthcare object based at least in part on the path object, wherein the routing rules are influenced by a manner in which the objects in the scene were discriminated;

routing, by the at least one processor, the healthcare object to a destination device according to the routing rules; and causing, by the at least one processor, the destination device to enable rendering of a user interface on a display in response to receiving the healthcare object.

2. The method of claim 1, wherein the routing rules are generated based on a confidence level associated with the discrimination, and wherein a low confidence level causes the routing rules to direct the healthcare object to an intermediate recipient before a final destination.

3. The method of claim 2, wherein the intermediate recipient comprises a subject matter expert.

4. The method of claim 1, wherein the routing rules are generated based on a number of data modalities used in the discrimination.

5. The method of claim 1, wherein the routing rules are generated based on at least one of a time at which the discrimination occurred or a location where the discrimination occurred.

6. The method of claim 1, wherein the routing rules are generated based on identities of entities involved with the discrimination.

7. The method of claim 1, wherein the routing rules comprise at least one of a priority indicator, an urgency indicator, a destination chain, a quality of service requirement, or a security requirement for the healthcare object.

8. The method of claim 1, further comprising determining, by the at least one processor, a level of encryption to apply to the healthcare object based on a discrimination measure of a corresponding scene object.

9. The method of claim 8, wherein a low discrimination measure results in a low level of encryption applied to the healthcare object.

10. The method of claim 1, wherein the path object further comprises metadata tags indicating the data modalities and algorithms applied during the discrimination.

11. The method of claim 1, wherein the set of discriminator characteristics comprises a vector of discriminator characteristics, the vector comprising multiple vector members, and each vector member corresponding to a different modality of data.

12. The method of claim 1, wherein generating the routing rules comprises applying routing policies associated with the healthcare object type to the path object, the routing policies dictating a destination chain for the healthcare object.

13. A system for routing healthcare objects, the system comprising:

a non-transitory computer readable memory configured to store computer-executable instructions; and at least one processor configured to execute the computer-executable instructions to:

receive, from at least one sensor, a digital representation of a scene;

derive a set of discriminator characteristics via execution of one or more discriminator algorithms on the digital representation according to data modalities within the digital representation;

generate a path object comprising indicators of data modalities used, algorithms applied, and confidence levels reflecting a process by which objects in the scene were discriminated;

discriminate objects in the scene by recognizing an object as a healthcare object type based on the set of discriminator characteristics;

instantiate a healthcare object from the recognized object according to the healthcare object type;

generate routing rules for the healthcare object based at least in part on the path object, the routing rules being influenced by a manner in which the objects in the scene were discriminated;

route the healthcare object to a destination device according to the routing rules; and cause the destination device to enable rendering of a user interface on a display in response to receiving the healthcare object.

14. The system of claim 13, wherein the at least one processor is configured to execute the computer-executable instructions to, when a confidence level associated with the discrimination satisfies routing criteria, insert an intermediate recipient into a destination chain of the routing rules before a final destination.

15. The system of claim 14, wherein the intermediate recipient comprises a subject matter expert.

16. The system of claim 13, wherein the routing rules comprise at least one of a priority indicator, an urgency indicator, a chain of recipients, a quality of service requirement, a required time of delivery, or a security credential.

17. The system of claim 13, wherein the at least one processor is configured to execute the computer-executable instructions to determine a level of encryption to apply to the healthcare object based on a discrimination measure of a corresponding scene object, the discrimination measure reflecting a degree of certainty of the discrimination.

18. The system of claim 13, wherein the path object further comprises indicators of at least one of a time at which the discrimination occurred, a location where the discrimination occurred, or identities of entities involved with the discrimination.

19. A non-transitory computer-readable medium storing computer-executable instructions which, when executed by at least one processor, cause the at least one processor to:

receive, from at least one sensor, a digital representation of a scene;

derive a set of discriminator characteristics via execution of one or more discriminator algorithms on the digital representation according to data modalities within the digital representation;

generate a path object indicating data modalities used, algorithms applied, and confidence levels associated with a process by which objects in the scene were discriminated;

discriminate objects in the scene by recognizing an object as a healthcare object type based on the set of discriminator characteristics;

instantiate a healthcare object from the recognized object according to the healthcare object type;

generate routing rules for the healthcare object based at least in part on the path object, the routing rules being influenced by a confidence level of the discrimination such that a low confidence level causes the routing rules to include an intermediate recipient in a routing chain before a final destination; and route the healthcare object according to the routing rules.

20. The non-transitory computer-readable medium of claim 19, wherein the instructions further cause the at least one processor to determine a level of security to apply to the healthcare object based on a discrimination measure of a corresponding scene object, the discrimination measure comprising a multi-valued measure where each value represents a different aspect of the discrimination.

* * * * *